(12) United States Patent
Luber

(10) Patent No.: US 8,384,994 B2
(45) Date of Patent: Feb. 26, 2013

(54) METHOD FOR OPERATING AN OPTICAL SYSTEM AND OPTICAL SYSTEM

(75) Inventor: Joachim Luber, St. Margrethen (CH)

(73) Assignee: Forstgarten International Holding GmbH, St. Gallen (CH)

( * ) Notice: Subject to any disclaimer, the term of this patent is extended or adjusted under 35 U.S.C. 154(b) by 889 days.

(21) Appl. No.: 12/096,496

(22) PCT Filed: Dec. 6, 2006

(86) PCT No.: PCT/EP2006/011718
§ 371 (c)(1),
(2), (4) Date: Nov. 21, 2008

(87) PCT Pub. No.: WO2007/065660
PCT Pub. Date: Jun. 14, 2007

(65) Prior Publication Data
US 2009/0135475 A1 May 28, 2009

(30) Foreign Application Priority Data
Dec. 8, 2005 (EP) .................................... 05026775

(51) Int. Cl.
*G02B 21/22* (2006.01)

(52) U.S. Cl. ....................................................... 359/380
(58) Field of Classification Search ................... 359/383
See application file for complete search history.

(56) References Cited

U.S. PATENT DOCUMENTS

| | | | |
|---|---|---|---|
| 5,307,202 A * | 4/1994 | Martino et al. | 359/363 |
| 7,738,016 B2 * | 6/2010 | Toyofuku | 348/240.1 |
| 8,027,095 B2 * | 9/2011 | Havens | 359/666 |

FOREIGN PATENT DOCUMENTS

DE         10323629         10/2004

* cited by examiner

*Primary Examiner* — Derek S Chapel
(74) *Attorney, Agent, or Firm* — McDonnell Boehnen Hulbert & Berghoff LLP

(57) ABSTRACT

The invention provides a microscope (2) as part of an optical system (1) used to spatially image an object in an image plane, and methods for its use, wherein the microscope (2) has at least one lens system assigned to a respective beam path (3, 4) and a converging lens arrangement (11) assigned to the beam path(s) (3, 4), wherein the at least one lens system includes a first lens arrangement (3a; 4a) and a second lens arrangement (3b; 4b) arranged between the first and the converging lens arrangement.

17 Claims, 2 Drawing Sheets

METHOD FOR OPERATING AN OPTICAL SYSTEM AND OPTICAL SYSTEM

Figure 1:
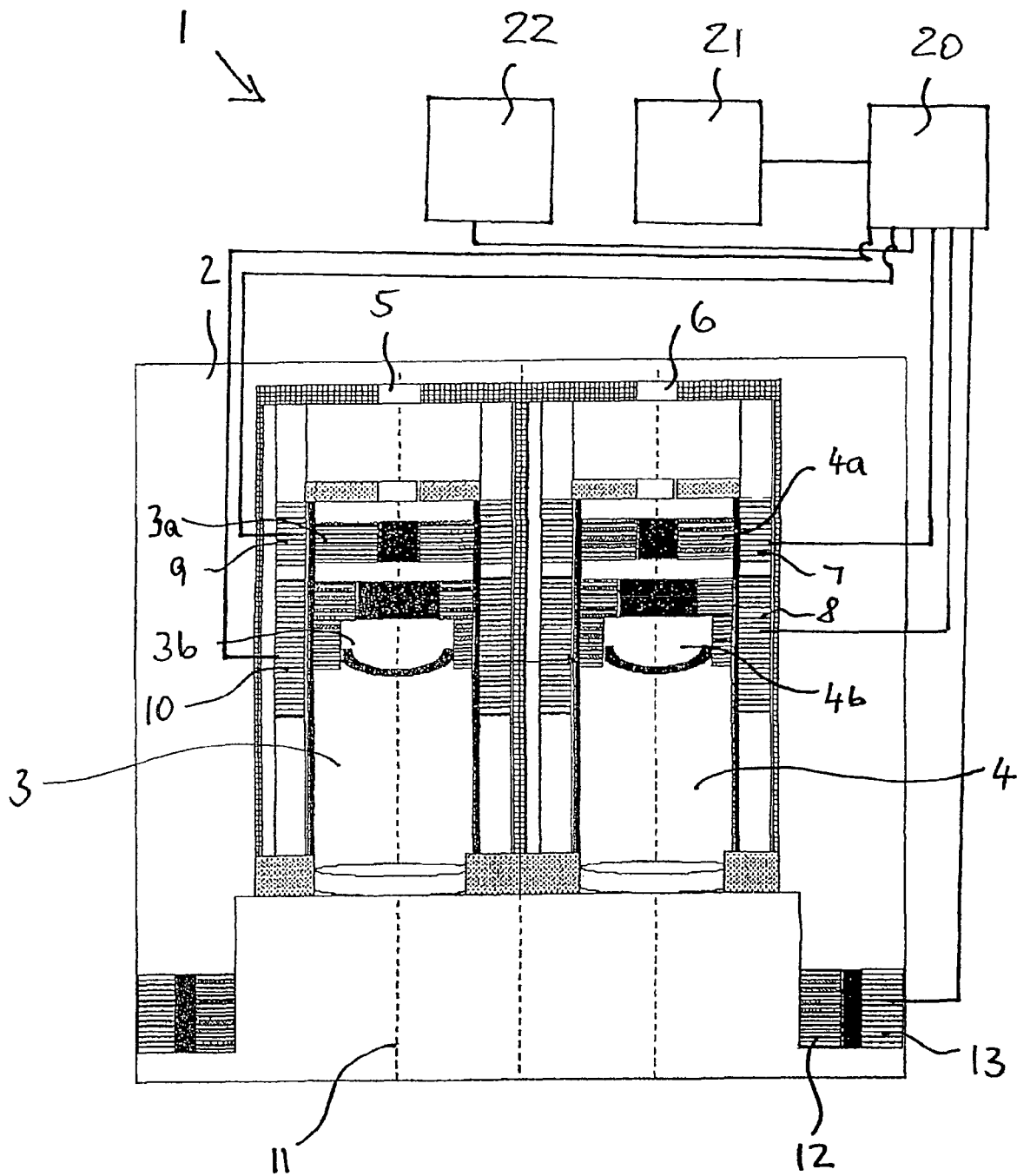

The invention relates to a method for operating an optical system and an optical system.

BACKGROUND OF THE INVENTION

Optical systems such as stereomicroscopes are used in most diverse applications for generating a spatial image of an object of study. Such optical systems are employed in medical surgical microscopes for example, to inspect a surgical area.

The spatial image of the object of study is generated using the stereomicroscope which involves a representative from the instrument class of reflected light microscopes. The object of study is illuminated from the outside. Usually two optical paths are formed which are on their part equipped in each case with a lens system. The optical axes of both optical paths run through an arrangement of collecting lenses being upstream of the lens systems in direction of the object of study. Both the lens systems and also the collecting lens arrangement can comprise several optical lenses. The various optical lenses are used to adjust a focus as well as a zoom factor of the stereomicroscope. For this purpose, the lenses are displaced individually or in groups along the respectively assigned optical axis.

The displacement of optical elements for adjustment of the focus or for the adjustment of the zoom factor can be performed with the aid of motor-powered adjustment devices which relocate the optical element to a designated position along the optical axis. In contrast to the equally known displacement of optical elements by hand such motor-powered adjustment devices are controlled by the user with an operation device, for example a controller regulating the voltage- or power supply. As long as the user switches on the operation device, the lens is displaced along the optical axis. This movement is stopped by the user by switching off the operation device.

In document DE 103 23 629 A1, a gliding field linear motor is described with which optical elements, for example an optical lens, arranged in a sleeve, can be displaced along the optical axis. This is achieved using a magnetic gliding field moving along the optical axis. The magnetic gliding field and, thus, also the displacement positions of the optical elements are adjustable very accurately. The known gliding field linear motor supports the miniaturization of optical systems.

SUMMARY OF THE INVENTION

It is the object of the invention to provide a method for operating an optical system with a microscope and an optical system, wherein the operating convenience is improved, especially with respect to the ease of use and to a directed positioning of optical elements within an optical canal.

The problem is solved according to the invention by a method for operating an optical system with a microscope according to independent claim 1 as well as an optical system with a microscope according to independent claim 11.

The invention comprises the thought to operate an optical system in a way that for changing a focus setting and/or zoom factor of the microscope in response to the input of a user, a desired focus setting and/or a desired zoom factor is generated automatically with the aid of motor-powered adjustment devices, by generating, in response to the registered input of a user, control signals in a controlling device according to stored pre-settings and which are transformed with the aid of the respective motor-powered adjustment devices into movements of the optical elements of the microscope. For this purpose, the stored pre-settings comprise electronic information about positions of the optical elements, specifically the lenses, of the microscope for defined focus settings and/or zoom factors. By this means the microscope can automatically be adjusted, depending on the registered user input, by accessing the stored pre-settings, so that a defined focus setting and/or a defined zoom factor is provided. The pre-settings were determined for the optical system in advance, for example, using measurements on an optical table and are stored in form of electronic data.

The user does not have to dislocate the optical elements along the optical axis and to search for an optimal positioning by himself, as is intended by the prior art. The user rather merely provides a desired focus setting and/or a desired zoom factor whereupon the optical system autonomously adjusts a focus/zoom factor setting, having regard to the stored pre-settings. The displacement of lenses by hand is also not necessary.

A suitable embodiment of the invention provides that a coarse focus adjustment is carried out during the adjustment of the focus setting by generating in the controlling device coarse controlling signals which are comprised in the controlling signals and which are transmitted from the controlling device to the motor-powered adjustment device of the collecting lens arrangement and by relocating the collecting lens arrangement with the aid of the motor-powered adjustment device of the collecting lens arrangement according to the coarse controlling signals. In this way, a separate coarse adjustment of the focus is made possible in an uncomplicated way, optionally as prestage for a subsequent fine adjustment of the focus.

In a preferred embodiment of the invention it can be intended that a fine focus adjustment is carried out during the adjustment of the focus setting by generating in the controlling device fine controlling signals which are comprised in the controlling signals and which are transmitted from the controlling device to the respective motor-powered adjustment device of the first lens arrangement in one or all optical paths and by displacing the first lens arrangement in one or all optical paths with the aid of the respective motor-powered adjustment device according to the fine controlling signals. Hereby an optimized focus adjustment using a fine gradation of the lens positioning is afforded.

In an advantageous embodiment of the invention, it is intended that the adjustment of the zoom factor is carried out by generating zoom controlling signals in the controlling device which are comprised in the controlling signals and which are transmitted from the controlling device to the respective motor-powered adjustment device of the second lens arrangement in one or all optical paths and by displacing the second lens arrangement in one or all optical paths with the aid of the respective motor-powered adjustment device according to the zoom controlling signals. Hereby the setting of a desired zoom factor which is easily selectable for the user is afforded. Thus, also users which are inexperienced in the usage of complex optical systems can offhandedly set a given zoom factor.

The amount of electronic information for the pre-settings data which are to be stored is minimized via an appropriate embodiment of the invention by carrying out in the controlling device an interpolation between selected pre-settings data of the stored pre-settings data during the generation of the controlling signals for adjusting the focus setting and/or the zoom factor. Using interpolation also focus settings and/ or settings of zoom factors can be carried out for which the related positioning of the lenses was not measured beforehand. Generally, a linear interpolation is performed between the pre-settings data used.

In an appropriate further development of the invention, it can be intended that the collecting lens arrangement, the first lens arrangement and/or the second lens arrangement are linearly displaced during relocation according to the control signals with the aid of the respective motor-powered adjustment device. To accomplish the relocation, preferably a linear motor is commissioned with the control signals. Such movement configuration during the relocation has the advantage that a precise displacement of the lenses can be accomplished. This improves the accuracy of the desired focus setting and/or of the desired zoom factor.

To make the spatial image of the object of study available for further processing, it is intended in an advantageous embodiment of the invention that the object of study is spatially mapped onto several electronic storage media which are assigned to an optical path, respectively. Similarly, the optical paths can obviously be directly made available to the eyes of the observer via so-called tubes.

A preferred advancement of the invention intends that a respective zoom factor is adjusted in the optical paths by displacing the first lens arrangement, the second lens arrangement and/or the collecting lens arrangement with the aid of the respective motor-powered adjustment device(s), wherein the respective adjustable zoom factors of the optical paths differ from each other. Thus, it is possible to generate a magnified view of one of the channels on a monitor or a photo camera, whereas the other channel features a smaller magnification, e.g. for the visual inspection of the surgeon, if the optical system is implemented as a stereomicroscope.

Preferably, the optical system comprises a stereomicroscope.

Motor-powered adjustment devices using a moving magnetic gliding field proved especially advantageous for an exact and finely graded displacement of lenses in the microscope as is described, e.g. in document DE 103 23 629 A1.

The embodiments of the invention in the dependent claims concerning the optical system with a microscope provide the advantages which are respectively commented in connection with the respective features in the dependent method claims.

DESCRIPTION OF PREFERRED EXAMPLES OF EMBODIMENTS OF THE INVENTION

Figure 2:
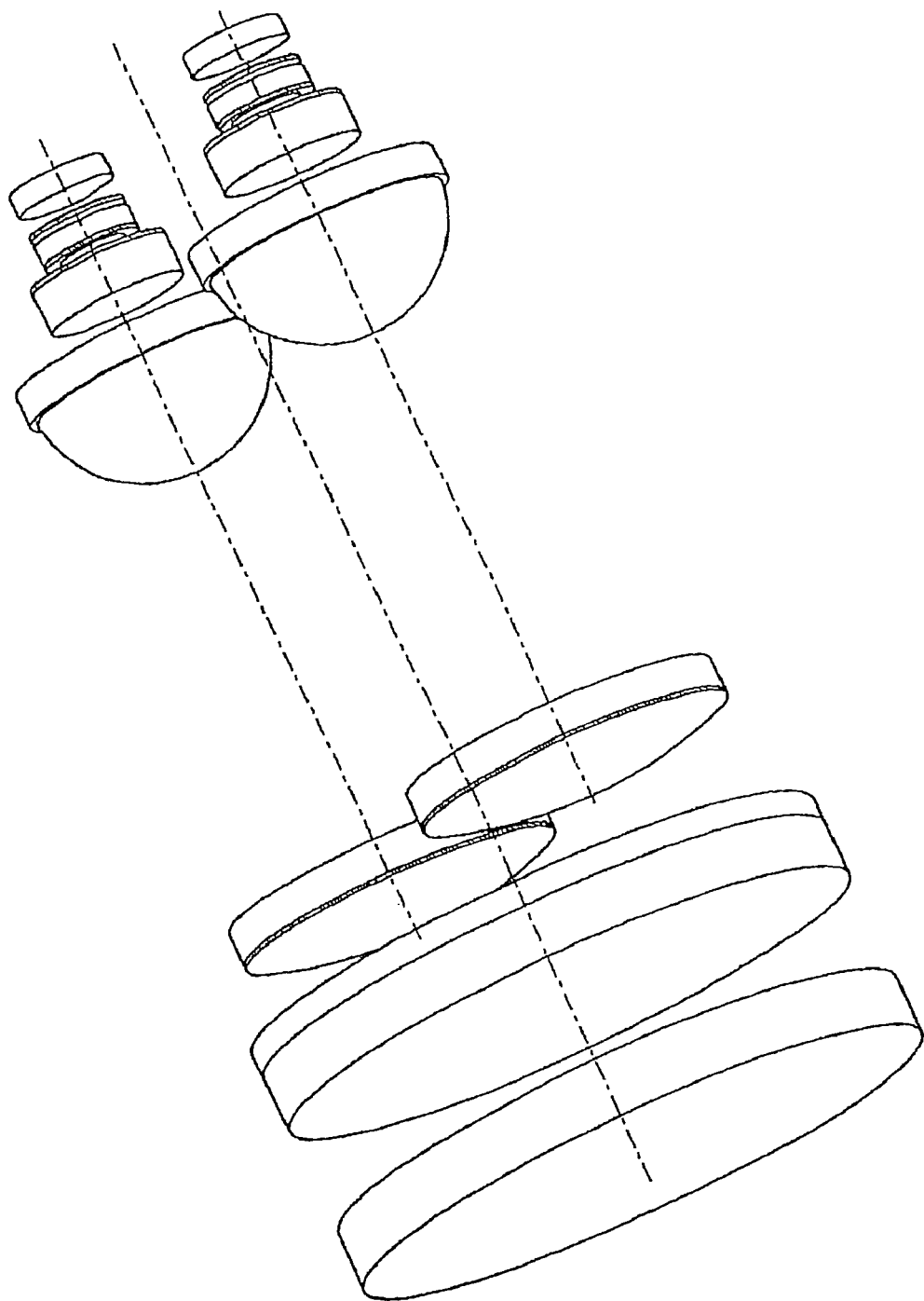

In the following, the invention will be exemplified more closely by means of examples with reference to the figures. Hereby shows:

FIG. 1 a schematic illustration of the optical system with a stereomicroscope in plain view; and FIG. 2 a perspective illustration of optical lenses of the stereomicroscope in the optical system according to FIG. 1.

FIG. 1 shows a schematic illustration of optical system 1 with a stereomicroscope 2. In the stereomicroscope 2 two optical paths 3, 4 are formed. With the aid of stereomicroscope 2 an object of study (not shown) is spatially imaged onto video chips 5, 6 using both optical paths 3, 4. The video chips 5, 6 serve as electronic memory for the spatial image so that image processing can be carried out subsequently.

Along the optical axis a first and a second lens arrangement 3a, 3b; 4a, 4b is arranged in both optical paths 3, 4 in each case. The first and the second lens arrangement 3a, 3b; 4a, 4b comprise in each case one or several optical lenses. The optical lenses are held in a respective retainer which are in turn displaceable along the respective optical axis using motor-powered adjustment parts 7, 8, 9, 10.

To both optical paths 3, 4 a collecting lens arrangement 11 is assigned, which is also held in a retainer 12. In retainer 12, the collecting lens arrangement 11 is relocatable with the aid of a further adjustment element 13.

The motor-powered adjustment elements 7, 8, 9, 10, 13 are coupled with a controlling device 20, so that controlling signals generated from the controlling device 20 can be transmitted to the motor-powered adjustment elements 7, 8, 9, 10, 13 to carry out a focus adjustment and/or an adjustment of a zoom factor of the stereomicroscope 2. The controlling device 20 on its part is connected with an input device 21, with which a user input is registered. The input device 21 concerns e.g. a touch pad or a keyboard as is known in the context of control panels.

The motor-powered adjustment elements 7, 8, 9, 10, 13 can be revolving field adjustment devices. Alternatively, the motor-powered adjustment elements 7, 8, 9, 10, 13 can concern electromagnetic gliding field linear motors for moving the optical elements. Such electromagnetic gliding field linear motor comprises an axial movable sliding sleeve which glides in a cladding tube and which contains at least one axially polarized permanent magnet as well as the optical element and the optical elements, respectively. Furthermore, an arrangement of at least three coils is provided which are wound around the cladding tube and which can generate through a separate variable supply of current a magnetic gliding field which is intensified and guided in concentrated form by magnetic reflux via a soft magnetic outer tube and soft magnetic armature pole pieces. The three phase travelling field is used to move the permanent magnet and the slide sleeve connected thereto in the axial direction. By interacting with the permanent magnet, the travelling field generates self holding forces that result in the armature location being locked down and in the optical elements being positionally stabilized by restoring forces. Using electromagnetic gliding field linear motors for the motor-powered adjustment devices according to the invention allows a most compact design of the optical system 1 according to the invention. For further details of such electromagnetic gliding field linear motors reference is made to the document DE 103 23 629 A1.

The overall length of the stereomicroscope 2 is reduced if for the fine focus adjustment not only the collecting lens arrangement 11 but also the motor-powered adjustment devices 3a, 4a are moved using the motor-powered adjustment element 13. A zoom factor of the stereomicroscope 2 is achieved via displacement of the second lens arrangement 3b, 4b. The second lens arrangements 3b, 4b are adjustable independently of each other, so that zoom factors which are different from each other can be adjusted at a given point in time in both optical paths 3, 4.

When a user input is registered with the aid of the input device 21 to adjust the focus setting and/or the zoom factor of the stereomicroscope 2, controlling signals are being subsequently generated in the controlling device 20 according to pre-settings data, which are electronically stored in a storage device 22 which is connected with the controlling device 20. Hereby it concerns electronic information pertaining to the positioning of the first lens arrangement 3a, 4a and the second lens arrangement 3b, 4b in one of both optical paths 3, 4 and/or of the collecting lens arrangement 11 for defined focus settings and/or zoom factors.

If it occurs that, after registering of the user input, for the desired focus setting and/or for the desired zoom factor no exact matching pre-settings data are stored, the controlling device 20 determines pre-settings data for neighbouring focus settings/zoom factors and linearly interpolates therefrom the information for generating the respective controlling signals.

FIG. 2 shows a perspective illustration of optical lenses of the first and the second lens arrangement 3a, 4a; 3b, 4b of the stereomicroscope 20 in the optical system according to FIG. 1.

The features of the invention which are disclosed in the present description, the claims and the figures can be of importance individually as well as in arbitrary combination for the realization of the invention in its various embodiments.

The invention claimed is:

1. Method for operating an optical system to spatially image an object of study in an image plane of a stereomicroscope comprised in the optical system, comprising:
   (a) registering a user input to adjust at least one of a focus setting and a zoom factor of a stereomicroscope using an input device, wherein the stereomicroscope comprises (i) at least a first lens system and a second lens system, where each lens system is assigned to a respective optical path, wherein each lens system comprises a first lens arrangement and a second lens arrangement; and (ii) a collecting lens arrangement assigned to the optical path of each lens system; wherein the second lens arrangement is positioned between the first lens arrangement and the collecting lens arrangement;
   (b) generating controlling signals assigned to the registered user input for adjusting at least one of the focus setting and the zoom factor in a controlling device coupled to the input device wherein the controlling signals are built according to pre-settings data which are stored in a storage device connected to the controlling device;
   (c) transmitting the controlling signals to one or several respective motor-powered adjustment devices for displacing at least one of the first lens arrangement, the second lens arrangement and the collecting lens arrangement;
   (d) adjusting at least one of the focus setting and the zoom factor of the stereomicroscope according to the controlling signals by displacing at least one of the first lens arrangement, the second lens arrangement and the collecting lens arrangement using the one or several respective motor powered adjustment device, wherein a respective zoom factor is adjusted in the optical path of each lens system by displacing at least one of the first lens arrangement, the second lens arrangement and the collecting lens arrangement using the respective motor-powered adjustment device, wherein the respective adjustable zoom factors of the optical path of each lens system are different from each other; and
   (e) where the method is characterized in that an interpolation is carried out in the controlling device between selected pre-settings data of the stored pre-settings data during the generation of the controlling signals for adjusting at least one of the focus setting and the zoom factor.

2. Method according to claim 1, characterized in that during the adjustment of the focus setting a coarse adjustment is carried out by generating in the controlling device coarse controlling signals comprised in the controlling signals and by transmitting them from the controlling device to the respective motor-powered adjustment device of the collecting lens arrangement and by displacing the collecting lens arrangement using the respective motor-powered adjustment device of the collecting lens arrangement according to the coarse controlling signals.

3. Method according to claim 1, characterized in that a fine focus adjustment is carried out during adjustment of the focus setting by generating in the controlling device fine controlling signals comprised in the controlling signals and by transmitting them from the controlling device to the respective motor-powered adjustment device of the first lens arrangement in the optical path of each lens system and by displacing the first lens arrangement in the optical path of each lens system using the respective motor-powered adjustment device according to the fine controlling signals.

4. Method according to claim 1, characterized in that the adjustment of the zoom factor is carried out by generating in the controlling device zoom controlling signals comprised in the controlling signals and by transmitting them from the controlling device to the respective motor-powered adjustment device of the second lens arrangement in the optical paths of each lens system and by transmitting the second lens arrangement in the optical paths of each lens system and by displacing the second lens arrangement in the optical paths of each lens system using the respective motor-powered adjustment device according to the zoom controlling signals.

5. Method according to claim 1, characterized in that at least one of the collecting lens arrangement, the first lens arrangement and the second lens arrangement is linearly displaced according to the controlling signals using the respective motor-powered adjustment device.

6. Method of claim 1, characterized in that in the respective motor-powered adjustment device a linear motor which effects the displacement of at least one of the collecting lens arrangement, of the first lens arrangement and of the second lens arrangement according to the controlling signals is acted upon by the controlling signals.

7. Method according to claim 1, characterized in that the one or several respective motor-powered adjustment devices are electromagnetic gliding field linear motors.

8. Method according to claim 1, characterized in that the object of study is spatially imaged onto several electronic storage media which are respectively assigned to the optical path of each lens system, and made directly available to the observer via tubes, or both.

9. Method of claim 1, wherein a respective zoom factor is adjusted in the optical paths by displacing at least one of the first lens arrangement, the second lens arrangement and the collecting lens arrangement with the aid of the respective motor-powered adjustment device(s), wherein the respective adjustable zoom factors of the optical paths differ from each other, such that a magnified view is produced in at least one of the optical paths and a smaller magnification view is produced in the other optical path.

10. Optical system with a stereomicroscope for imaging an object of study, comprising:
   (a) a stereomicroscope comprising (i) at least a first lens system and a second lens system, where each lens system is assigned to a respective optical path, wherein each lens system comprises a first lens arrangement and a second lens arrangement; and (ii) a collecting lens arrangement assigned to the optical path of each lens system; wherein the second lens arrangement is positioned between the first lens arrangement and the collecting lens arrangement;
   (b) an input device for receiving a user input for at least one of a focus setting to be adjusted and a zoom factor to be adjusted of the stereomicroscope;
   (c) a controlling device which is coupled to an input device and with which controlling signals for adjusting at least one of the focus setting and the zoom factor are producible which are assigned to the registered user input, wherein the controlling signal pre-settings data are respectively generated which are stored in advance in a storage device connected with the controlling device;

(d) a respective motor-powered adjustment device of at least one of the first lens arrangement, the second lens arrangement and the collecting lens arrangement, with which at least one of the first lens arrangement, the second lens arrangement and the collecting lens arrangement are adjustable according to the controlling signals;

(e) a transmitting device for transmitting the controlling signals to one or several of the respective motor-powered adjustment devices of at least one of the first lens arrangement, the second lens arrangement and the collecting lens arrangement, wherein by using the respective motor-powered adjustment device at least one of the collecting lens arrangement, the first lens arrangement and the second lens arrangement in the optical path of each lens system a respective zoom factor is adjustable, wherein the respectively adjustable zoom factors of the optical path of each lens system are different from each other;

(f) wherein the controlling device comprises interpolation means with which an interpolation between selected pre-settings data of the stored pre-settings data can be carried out during the generation of the controlling signals in the controlling device for adjusting at least one of the focus setting and the zoom factor.

11. Optical system according to claim 10, characterized in that the respective motor-powered adjustment device of the collecting lens arrangement is assigned to a coarse focus adjustment so that coarse controlling signals comprised in the controlling signals and received by the controlling device are processible with the respective motor-powered adjustment device of the collecting lens arrangement.

12. Optical system according to claim 10, characterized in that the respective motor-powered adjustment device of the first lens arrangement in the optical paths of each lens system is assigned to a fine focus adjustment, so that fine controlling signals comprised in the controlling signals and received from the controlling device for adjusting the fine focus setting are processible with the respective motor powered adjustment device of the first lens arrangement in the optical paths of each lens system.

13. Optical system according to claim 10, characterized in that the respective motor-powered adjustment device of the second lens arrangement in the optical paths of each lens system is assigned to the zoom factor so that zoom controlling signals comprised in the controlling signals and received from the controlling device for adjusting the zoom factor are processible with the respective motor-powered adjustment device of the second lens arrangement in the optical paths of each lens system.

14. Optical system according to claim 10, characterized in that the respective motor-powered adjustment device of the collecting lens arrangement of at least one of the first lens arrangement and of the second lens arrangement comprises a linear motor.

15. Optical system according to claim 10, characterized in that at least one of the collecting lens arrangement, the first lens arrangement and the second lens arrangement are arranged in one or several sleeves and that they are displaceable using a moveable magnetic gliding field in one or all sleeves, respectively.

16. Optical system according to claim 10, characterized in that several electronic storage media which are assigned in each case to the optical path of each lens system for receiving the spatial image of the object of study.

17. Optical system according to claim 10, characterized in that the respective motor-powered adjustment device of the collecting lens arrangement of at least one of the first lens arrangement and of the second lens arrangement are powered by a revolving field.

* * * * *